(12) United States Patent
Pierry et al.

(10) Patent No.: US 7,684,931 B2
(45) Date of Patent: *Mar. 23, 2010

(54) GAS MONITORING SYSTEM AND SIDESTREAM GAS MEASUREMENT SYSTEM ADAPTED TO COMMUNICATE WITH A MAINSTREAM GAS MEASUREMENT SYSTEM

(75) Inventors: Anthony T. Pierry, Plantsville, CT (US); David R. Rich, Glastonbury, CT (US)

(73) Assignee: RIC Investments, LLC, Wilmington, DE (US)

( * ) Notice: Subject to any disclaimer, the term of this patent is extended or adjusted under 35 U.S.C. 154(b) by 1205 days.

This patent is subject to a terminal disclaimer.

(21) Appl. No.: 11/243,001

(22) Filed: Oct. 4, 2005

(65) Prior Publication Data

US 2006/0052950 A1    Mar. 9, 2006

Related U.S. Application Data (63) Continuation-in-part of application No. 10/781,382, filed on Feb. 18, 2004, now Pat. No. 6,954,702.

(60) Provisional application No. 60/449,428, filed on Feb. 21, 2003.

(51) Int. Cl.
*G01N 33/00* (2006.01)

(52) U.S. Cl. .............................. 702/22; 702/23; 702/24; 702/32; 702/122; 600/532; 600/538; 422/94

(58) Field of Classification Search .................... 702/22, 702/23, 24, 32, 122; 73/23.2, 23.22, 23.3, 73/23.35, 23.36, 23.37, 23.41; 600/529, 600/531, 532, 533, 534, 538; 422/94
See application file for complete search history.

(56) References Cited

U.S. PATENT DOCUMENTS

| 4,177,381 | A |   | 12/1979 | McClatchie et al. |
| 4,692,621 | A |   | 9/1987  | Passaro et al. |
| 4,907,166 | A | * | 3/1990  | Corenman et al. ............ 702/30 |
| 4,914,720 | A |   | 4/1990  | Knodle et al. |
| 4,958,075 | A |   | 9/1990  | Mace et al. |
| 5,111,827 | A |   | 5/1992  | Rantala |
| 5,282,473 | A |   | 2/1994  | Braig et al. |
| 5,464,982 | A | * | 11/1995 | Drucker et al. .............. 250/343 |

(Continued)

FOREIGN PATENT DOCUMENTS

WO    WO 99/20984    4/1999

OTHER PUBLICATIONS

PerkinElmer optoelectronics, "Digital Mainstream CO2 Sensor", 2001.

(Continued)

*Primary Examiner*—Carol S Tsai (57) ABSTRACT

A method and apparatus for interfacing a plurality of gas measurement systems, including a mainstream and a sidestream gas measurement system, to a host system via an interface unit. The present invention also pertains to a sidestream gas measurement system that output signals emulating the signals output by a mainstream gas measurement system or portion thereof, so that the sidestream gas measurement system can seamlessly communicate with a host system configured to communicate with a mainstream gas measurement system or a portion thereof.

8 Claims, 4 Drawing Sheets

U.S. PATENT DOCUMENTS

| | | | |
|---|---|---|---|
| 6,632,402 B2* | 10/2003 | Blazewicz et al. | 422/84 |
| 6,709,405 B2* | 3/2004 | Jonson | 600/538 |
| 6,828,910 B2 | 12/2004 | VanRyzin et al. | |
| 2003/0190262 A1* | 10/2003 | Blazewicz et al. | 422/94 |
| 2003/0191405 A1* | 10/2003 | Rich et al. | 600/532 |
| 2004/0069304 A1* | 4/2004 | Jam | 128/204.18 |
| 2004/0256560 A1* | 12/2004 | Russell | 250/338.5 |
| 2004/0267151 A1 | 12/2004 | Eckerbom | |

OTHER PUBLICATIONS

Supplementary European Search Report, May 11, 2007.

* cited by examiner

GAS MONITORING SYSTEM AND SIDESTREAM GAS MEASUREMENT SYSTEM ADAPTED TO COMMUNICATE WITH A MAINSTREAM GAS MEASUREMENT SYSTEM

CROSS-REFERENCE TO RELATED APPLICATIONS

This application is a Continuation-in-Part (CIP) of U.S. patent application Ser. No. 10/781,382 filed Feb. 18, 2004, now U.S. Pat. No. 6,954,702, which claims priority under 35 U.S.C. § 119(e) from provisional U.S. patent application No. 60/449,428 filed Feb. 21, 2003, the contents of which are incorporated herein by reference.

BACKGROUND OF THE INVENTION

1. Field of the Invention

The present invention pertains to a method and apparatus for interfacing a plurality of Gas Measurement Systems to a Host System via an interface unit, and to a sidestream Gas Measurement System that is capable of communicating with a Host System that is specifically configured to communicate with a mainstream Gas Measurement System.

2. Description of the Related Art

Respiratory Gas Monitoring Systems typically include gas sensing, measurement, processing, communication, and display functions. They are generally classified by operating modality as either diverting (i.e., sidestream) or non-diverting (i.e., mainstream). A diverting Gas Measurement System transports a portion of the sampled gases from the sampling site through a sampling tube to the Sample Cell, where the constituents of the gas are measured by a Gas Sensor. The sampling side is typically a in breathing circuit coupled to the patient's airway or at a location near the patient's airway. A non-diverting Gas Measurement System, on the other hand, does not transport gas away from the breathing circuit or the patient's airway, but measures the gas constituents passing through a Sample Cell disposed in the breathing circuit.

Figure 1:
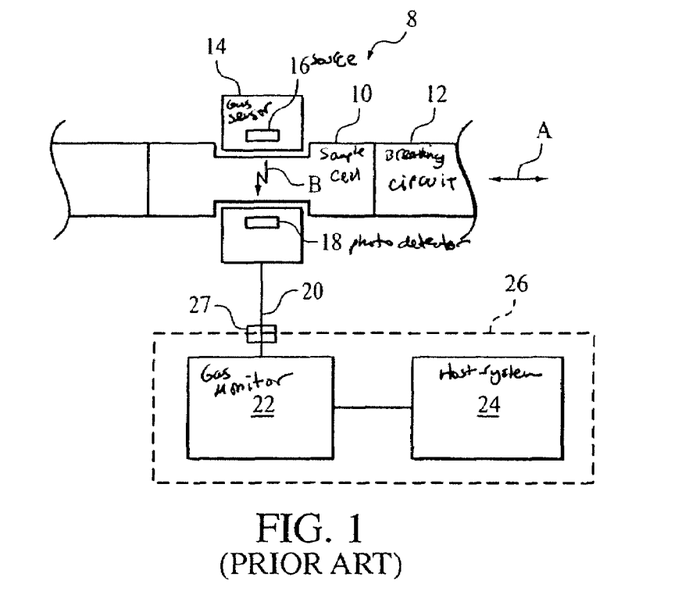
FIG. 1 is a schematic diagram of a conventional mainstream Gas Measurement System.

An example of a conventional mainstream Gas Measurement System 8 is schematically illustrated in FIG. 1. Mainstream Gas Measurement System 8 includes a Sample Cell 10 disposed in a breathing circuit 12 such that gas delivered to and/or received from the patient, as indicated by arrow A, passes through the Sample Cell. A Gas Sensor 14 coupled to the Sample Cell produces a detected or measured signal, e.g., a voltage, indicative of the concentration of a gas constituent in the gas sample in the Sample Cell. Gas Sensor 14 communicates with Sample Cell 10 placed at the breathing circuit and includes the components required to output a detected signal corresponding to a property of the gas to be measured.

For example, in a conventional mainstream Gas Measurement System that is capable of measuring carbon dioxide, Gas Sensor 14 includes a source 16 that emits infrared radiation, as indicated by arrow B, encompassing an absorption band for carbon dioxide. The infrared radiation is transmitted along a path that is normal to the flow path of the respiratory gas stream through the Sample Cell. Gas Sensor 14 in this conventional system further includes photodetectors 18 that measure the transmitted radiation. Carbon dioxide in the sample gas absorbs this radiation at some wavelengths and passes other wavelengths.

A multi-conductor lightweight, flexible cable 20 transmits the detected signals output by photodetectors 18 to a Gas Monitor 22 from which the partial pressure of carbon dioxide $CO_2$ is calculated. In a conventional mainstream system, the Gas Monitor is a stand-alone unit contained within a housing 26 that includes a terminal 27 to which cable 20 is selectively coupled. Within housing 26, the Gas Monitor includes processing elements that convert the detected signal from the Gas Sensor into a value, such as transmittance, that is used to produce an indication of the concentration of a particular gas constituent in the gas sample within the Sample Cell. This value indicative of the concentration of the gas under analysis is provided to a Host System 24 also contained in housing 26, which uses this information in any one of a variety ways. For example, the Host System may display the indication of the designated gas as a waveform or as a value in partial pressure units, such as mmHg or concentration in units, such as a percent (%). The Host System can use the indication to calculate other parameters, which can then be displayed or communicated to another system, such as a central station.

In the present example, the calculated $CO_2$ partial pressure is typically graphically displayed in the form of a capnogram via an output device serving as the Host System, such as a display provided on the exterior of the housing 26. Thus, Gas Monitor 22 contains the processing elements that control the operation of Gas Sensor 14 and provide the gas measurement functions to the Host System based on the output signals from the Gas Sensor. An example of such a conventional mainstream Gas Measurement System is shown in U.S. Pat. No. 4,914,720 issued to Knodle et al.

An advantage of a mainstream Gas Measurement System is that the placement of the Sample Cell directly at the breathing circuit results in a "crisp" gas concentration waveform that more faithfully reflects, in real-time, the varying partial pressure of the measured gas, such as carbon dioxide, within the airway that is generally possible using a sidestream approach. In addition, locating the Sample Cell, which is also referred to as a cuvette or airway adapter, in the respiratory gas stream obviates the need for gas sampling and scavenging as required in a sidestream Gas Measurement System.

Figure 2:
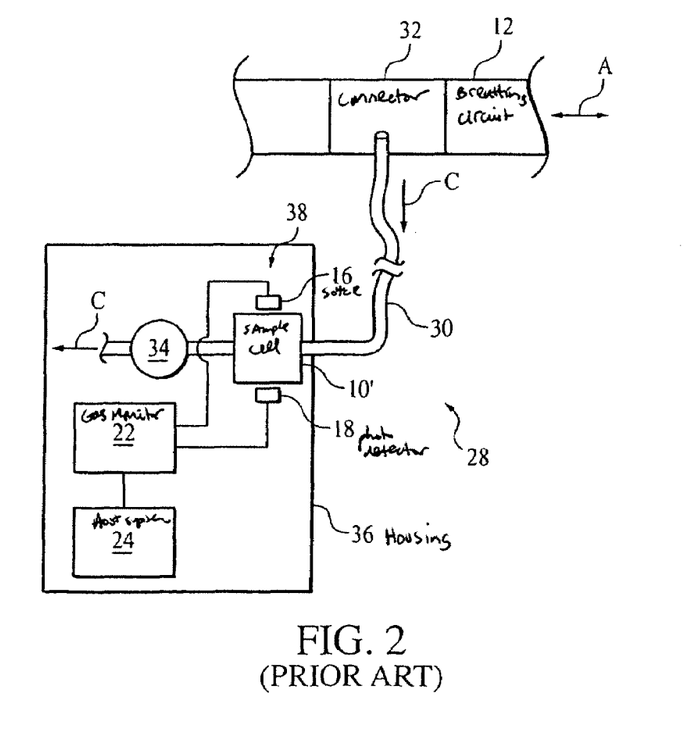
FIG. 2 is a schematic diagram of a conventional sidestream Gas Measurement System.

As example of a conventional sidestream Gas Measurement System 28 is shown in FIG. 2. Sidestream Gas Measurement System 28 utilizes a long sampling tube 30 connected to an adapter 32 connected in line in breathing circuit, such as a T-piece connected at the endotracheal tube or mask connector. It is also known to use a nasal canula as the gas collection element in a conventional sidestream system so that the gas is taken directly at the patient's airway. The sample gas is continuously aspirated from the breathing circuit or the nasal canula through sampling tube 30, as indicated by arrow C, and into a Sample Cell 10' at sample flow rates ranging from 50 to 250 ml/min. A pump 34 is typically provided to draw the gas into the Sample Cell from the gas sample site.

Sample Cell 10' is contained in a housing 36, which also contains both a Gas Sensor, generally indicated at 38, and a Gas Monitor 22. As with a mainstream system, the Gas Sensor in the sidestream Gas Measurement System includes components that provide a detected signal indicative of the concentration of a gas constituent in the gas sample in the Sample Cell, such as source 16 and emitter photodetectors 18. Similarly, the Gas Monitor in the sidestream Gas Measurement System includes the processing elements that convert the detected signal from the Gas Sensor into a value used to produce an indication of the concentration of a particular gas constituent. This value is provided to Host System 24, where it is typically displayed on a display provided on housing 36. Examples of conventional sidestream Gas Measurement Systems are taught in U.S. Pat. No. 4,692,621 to Passaro et al.; U.S. Pat. No. 4,177,381 to McClatchie, and U.S. Pat. No. 5,282,473 to Braig et al.

A large installed base of mainstream Gas Measurement Systems exist. However, a growing number of mainstream Gas Measurement System users desire or require the use a sidestream Gas Measurement System. These users seek a simple and easy solution to add the sidestream gas measurement capability to their existing patient monitor inventory without having to replace completely or partially the existing mainstream Gas Measurement Systems. However, existing mainstream Gas Measurement Systems do not allow users to easily add the sidestream sampling function, because they are specifically configured for mainstream operation.

Some manufactures have addressed this dilemma by providing a gas monitoring system that includes both the mainstream and sidestream functionality in a single enclosure. Of course, this approach is relatively expensive. It is also known to use a mainstream Gas Measurement System in a sidestream-type gas scavenging system. For example, U.S. Pat. No. 4,958,075 to Mace et al. ("the '475 patent") teaches providing a sidestream Gas Measurement System that includes most of the hardware required by a sidestream Gas Measurement System, such as a long tube, a Sample Cell disposed along the length of the tube, and a pump for drawing gas into the tube. However, instead of providing a Gas Sensor in the housing to which the Sample Cell attaches, as done in the conventional device shown in FIG. 1, the system taught by the '475 patent provides a mainstream type Gas Sensor coupled to the Sample Cell. In effect, the '475 patent teaches moving the Gas Sensor functions of a sidestream system out of the housing containing the Gas Monitor functions. It can be appreciated, that this approach still requires the use of a specialized adapter, which is connected to a pump, as well as valving, and control circuitry in the same box.

It is desirable to permit users of existing mainstream Gas Measurement Systems to add the sidestream gas measurement capability in a manner that permits their investment in mainstream Gas Measurement Systems to be preserved, while allowing addition of the sidestream gas measuring feature, as needed. Additionally, it is further desirable to permit users to not be burdened with having to employ complete systems, or a burdened mainstream Gas Measurement System, in order to gain the advantages of mainstream gas measurement, while permitting the use of sidestream gas measurement.

SUMMARY OF THE INVENTION

Accordingly, it is an object of the present invention to provide a Respiratory Gas Monitoring System that overcomes the shortcomings of conventional gas monitoring systems. This object is achieved according to one embodiment of the present invention by providing a Respiratory Gas Monitoring System that includes an interface unit having an input coupling and an output. The output is adapted to communicate with a Host System in any conventional manner. The Respiratory Gas Monitoring System further includes a plurality of Gas Measurement Systems. Each Gas Measurement System is adapted to be placed in fluid communication with an airway of a patient to measure at least one respiratory gas. In addition, each Gas Measurement System has an output coupling that is adapted to be removably coupled to the input coupling of the interface unit. Each Gas Measurement System also includes a processor that determines, from the respiratory gas, at least one respiratory variable of a patient and provides an output to the Host System via the interface unit. It can be appreciated that this Respiratory Gas Monitoring System provides a convenient technique to interface a plurality of gas sensing technologies, e.g., sidestream, mainstream, or both, to a single interface unit, which, in turn, communicates with a Host System.

It is yet another object of the present invention to provide a method of respiratory gas monitoring that does not suffer from the disadvantages associated with conventional gas monitoring techniques. This object is achieved by providing a method that includes providing an interface unit having an input coupling and an output and providing a plurality of Gas Measurement Systems. Each Gas Measurement System has an output coupling and processing elements for determining, from the respiratory gas, at least one respiratory variable of a patient. The method further includes the step of selectively coupling one of the plurality of Gas Measurement Systems to the interface unit by coupling the output coupling of an associated Gas Measurement System with the input coupling of the interface unit. In this manner, any type of Gas Measurement System can be coupled to a Host System via the interface device.

It is a further object of the present invention to provide a sidestream Gas Measurement System that is capable of seamlessly communicating with a Host System configured to communicate with a mainstream Gas Measurement System or a portion thereof. This object is achieved by providing a sidestream Gas Measurement System that includes a Sample Cell that is either integral with or removably connected to a housing via a sample cell connector disposed on the housing. A Gas Sensor in the housing communicates with the Sample Cell and outputs a signal indicative of a property of a gas in the Sample Cell. The sidestream Gas Measurement System also includes a controller that receives the signal from the Gas Sensor and uses it to generate an output signal. This output signal is also formatted by the controller to simulate the signals output by a mainstream Gas Measurement System or to simulate the signals output by a portion of a mainstream Gas Measurement System. A communication element, operatively coupled to the controller, interfaces the sidestream Gas Measurement System with a Host System.

It is still further object of the present invention to provide a method of sidestream gas monitoring that permits the user to seamlessly use a sidestream Gas Measurement System with a Host System configured to communicate with a mainstream Gas Measurement System. This object is achieved by providing a method that includes: (1) connecting a first conduit to an airway of a patient, either directly via a cannula or indirectly through a breathing circuit, (2) communicating a flow of gas through the first conduit to a Sample Cell, (3) measuring a property of gas in the Sample Cell via a Gas Sensor operatively coupled to the Sample Cell, (4) emulating signals provided by a mainstream Gas Measurement System or portion thereof including the measured property, and (5) providing the emulated signals to a Host System configured to interface with a mainstream Gas Measurement System. In this manner, the sidestream Gas Measurement System can communicate with a mainstream Gas Measurement System or component thereof.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 3:
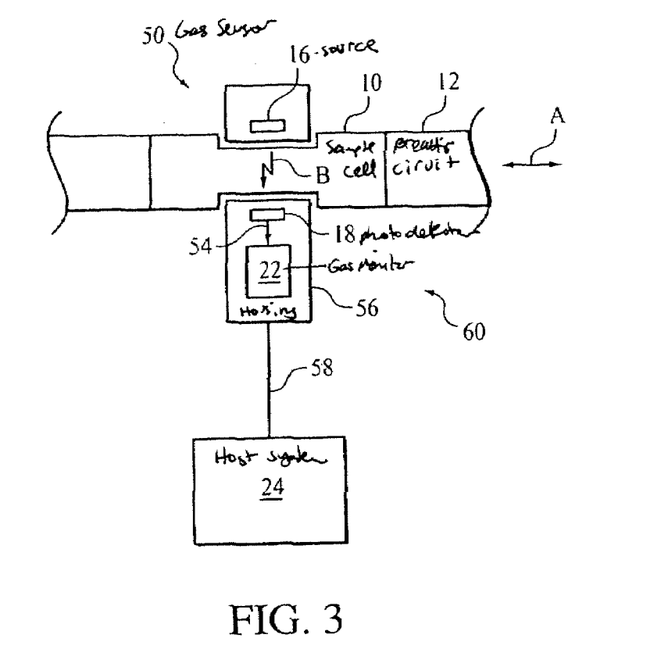
FIG. 3 is a schematic diagram of another embodiment of a mainstream Gas Measurement System suitable for use with the present invention.

A. Respiratory Gas Monitoring System With an Interface Unit for a Mainstream or a Sidestream Gas Measurement System The present invention provides a convenient technique to interface a plurality of gas sensing technologies to a common Host System by means of a single interface unit. More specifically, one embodiment of the present invention contemplates providing an interface unit that is adapted to couple to any type of Gas Measurement System, i.e., mainstream or sidestream. An output of the interface unit is coupled to a Host System. In this manner, the interface unit allows virtually any type of Gas Measurement System to communicate with a common Host System. FIGS. 1 and 2 schematically illustrate two configurations of conventional Gas Measurement Systems that can be connected to such an interface unit. FIG. 3 schematically illustrates and FIG. 4 is a perspective view of another embodiment of a mainstream Gas Measurement System 60 adapted to be coupled to the interface unit.

Figure 4:
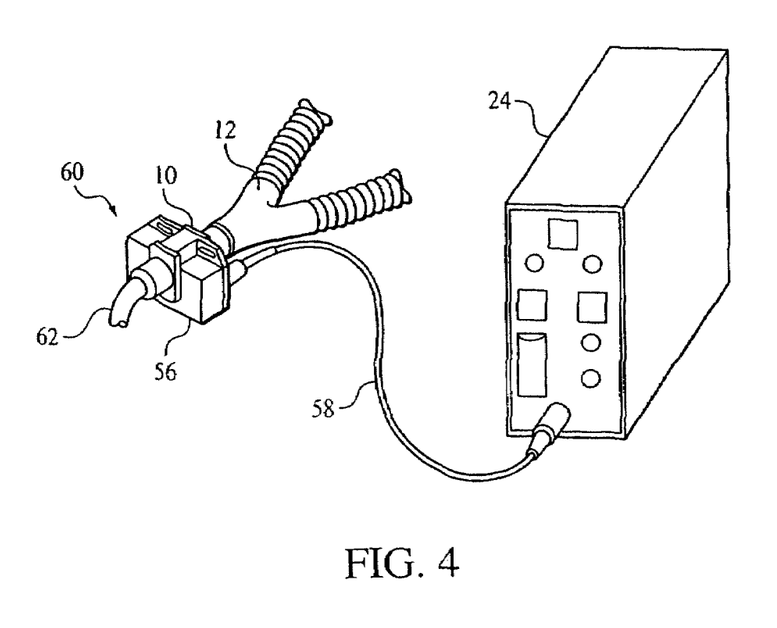
FIG. 4 is a perspective view of the mainstream Gas Measurement System of FIG. 3.

As shown in FIGS. 3 and 4, mainstream Gas Measurement System 60 includes a Sample Cell 10 disposed in breathing circuit 12 such that gas delivered to and/or received from the patient, as indicated by arrow A, passes through the Sample Cell. As with a conventional mainstream system, a Gas Sensor, generally indicated at 50, is coupled to the Sample Cell. Gas Sensor 50 includes components, such as source 16 and detector 18, necessary to produce a detected signal 54 indicative of the concentration of a gas constituent in the gas sample in the Sample Cell. Unlike the conventional mainstream Gas Measurement System shown in FIG. 1, a Gas Monitor 22 is incorporated into the same housing 56 containing the Gas Sensor. Gas Monitor 22 includes processing elements that convert the detected signal from the Gas Sensor into a value, such as transmittance, that is used to produce an indication of the concentration of a particular gas constituent in the gas sample within the Sample Cell. This value indicative of the concentration of the gas under analysis is provided to a Host System 24 via a communication link 58. The Host System uses this information from Gas Monitor 22 in the same manner as a Host System associated with a conventional mainstream or sidestream Gas Measurement System.

In the embodiment of FIGS. 3 and 4, the mainstream Gas Measurement System, generally indicated at 60 and comprising the Gas Sensor Gas Monitor subsystems, is entirely contained within housing 56, which is selectively attachable to Sample Cell 10. To be commercially viable, such a mainstream Gas Measurement System must be sufficiently small in size and lightweight as not to interfere with patient and/or ventilator management. With electronics manufacturing methods, as well as careful thermal and optical design, such a mainstream Gas Measurement System is possible. The present invention contemplates that communication link 58 is a conventional electrical cable, a specialized cable, or a wireless link using any technologies known in the art, including but not limited to infrared and RF links. Communication link 58 may also communicate, either via Host System 24 or directly, to a wired network, a wireless network, or both, including but not limited to a wide-area network (e.g., using 802.11b and 802.11g), personal area networks (e.g., Bluetooth), and body area networks (e.g., Zigbee).

An exemplary application of the mainstream Gas Measurement System for carbon dioxide is monitoring an intubated patient receiving mechanical ventilation. To monitor in such circumstances, Sample Cell 10 is placed between an endotracheal tube 62 inserted into the patient's trachea and the wye portion of breathing circuit 12 connected to a mechanical ventilator (not shown). The clinical indications for monitoring a patients carbon dioxide are well known in the art and have been reviewed in articles in general medical journals such as the New England Journal of Medicine as well as specific journals covering specialties such as anesthesiology, critical care, respiratory care, and emergency medicine.

It can be appreciated that placing the processing elements of the Gas Monitor in the same housing with the Gas Sensor elements reduces the complexity and cost of the stand-alone unit, i.e., the Host System. For example, in a conventional mainstream Gas Measurement System, the stand-alone unit, which is indicated by dashed line 26 in FIG. 1, must include the processing elements of Gas Monitor 22, as well as the components of Host System 24. In the embodiment of FIGS. 3 and 4, however, the stand-alone unit need only include the components of Host System 24. This enables the user to keep a low cost interface, i.e., Host System 24, that is suitable for use with a detachable Gas Measurement System. In addition, the user need not replace the Host System if upgrades to the Gas Sensor or Gas Monitor components are made.

While FIGS. 3 and 4 illustrate an exemplary embodiment of a mainstream Gas Measurement System, the present invention contemplates providing a sidestream Gas Measurement System in a similar manner so that the Gas Sensing and Gas Monitoring components are provided in a housing separate from the housing containing the Host System components. An embodiment in which the sub-systems of the sidestream Gas Measurement System are contained within a common housing that is either selectively attached to the Sample Cell or integrated with the Sample Cell may interface to the same Host System 24 as the mainstream Gas Measurement System. The sampling means, often a miniature pump, may be also contained within the housing of the Host System or the housing of the Gas Sensor and Gas Monitor.

Figure 5:
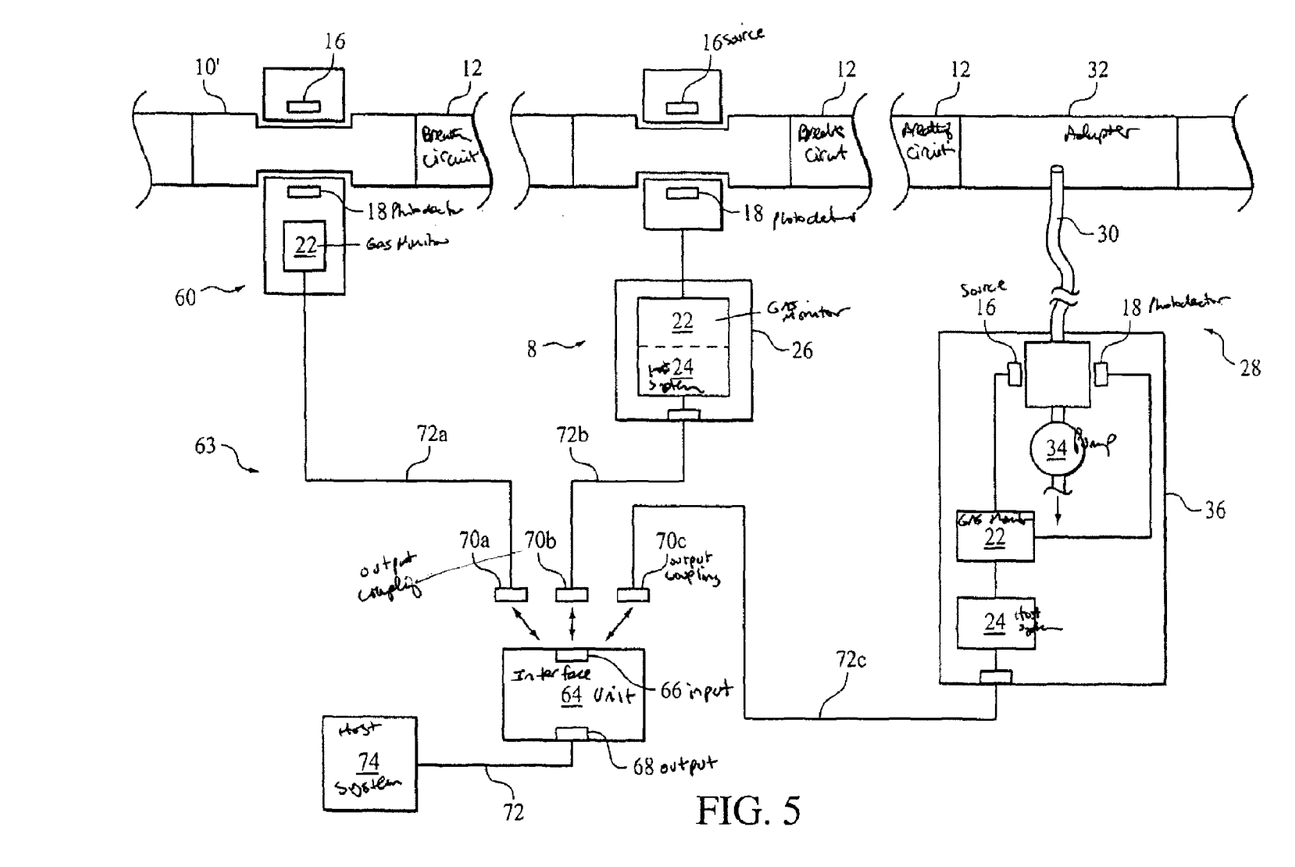
FIG. 5 is a schematic diagram of a Gas Monitoring System according to the principles of the present invention.

FIG. 5 is a schematic diagram of a Gas Monitoring System 63 according to the principles of the present invention, in which an interface unit 64 is provided that is adapted to couple to any type of Gas Measurement System, i.e., mainstream or sidestream, such as those illustrated in FIGS. 1-4, to form the Gas Monitoring System. Interface unit 64 have an input coupling 66 and an output 68. Each Gas Measurement System 60, 8, and 28 has an output coupling 70a, 70b, and 70c that is adapted to be removably coupled to input coupling 66 of interface unit 64. A communication link 72a, 72b, and 72c, in the form of a hardwired connection is provided between each Gas Measurement System and input coupling 66 to connect each Gas Measurement System with the interface unit.

The present invention also contemplates that communication link 72a, 72b, and 72c may be a wireless connection. In which case, the input coupling is a receiver adapted to receive each different type of wireless transmission.

It is to be understood that interface unit 64 can include only one input coupling 66, so that only one Gas Measurement System can be connected to it at any given time. On the other hand, the present invention also contemplates providing more than one input couplings on the interface unit so that more than one Gas Measurement System can be coupled to the interface unit at a time. In which case, software in the interface unit, Host System 74, or Gas Measurement Systems should be provided to allow the system to determine or control which Gas Measurement System is presently communicating with the Host System. This communication control function can also be accomplished via hardware, such as with a switch provided on interface unit 64 to selectively activate one of the plurality of the input couplings. Additionally, it is contemplated that Interface Unit 64 may provide input couplings for other types of measurement systems that measure a physiological parameter of a patient, such as a pulse oximeter, blood pressure monitor, motion detector, effort belt, temperature sensor, etc.

Interface unit 64 communicates with a Host System 74 via a communication link 72. Host System 74 provides the display and/or communication functionality to allow the output of the Gas Measurement System 60, 8, or 28 to be displayed, printed, downloaded, communicated, or otherwise transferred to a user. Communication link 72 is any conventional communication technique, such as hardwired or wireless. In this manner, interface unit 64 effectively allows any type of Gas Measurement System, i.e., mainstream, sidestream, or a hybrid thereof, to communicate with a Host System so that a value indicative of the respiratory gas under analysis is provided to the Host System for analysis, display, communication, or any combination thereof. An advantage of this Gas Monitoring System is that any type of conventional Gas Measurement System can be coupled to interface unit 64, so that users need not purchase specialized gas monitoring systems.

Host System 74 can be itself be a communication network or a node that communicates with a communication network. As noted above, the communication link to Host System can be hardwired or wireless. In addition, the communication link between the Gas Monitoring System and the Host System can be hardwired or wireless.

It should be noted that the respiratory gases to which the present invention applies include, but are not limited to, gases associated with respiration (i.e., oxygen and carbon dioxide), gases associated with anesthesia (i.e., nitrous oxide and halogenated agents), gases associated with therapy (i.e., helium/oxygen mixtures and nitric oxide) and gases or substances present in the breath known as markers of diseases or physiological processes (i.e., nitric oxide). In short, the Gas Monitoring System of the present invention is capable of measuring the same gasses as a conventional sidestream or mainstream Gas Measurement System.

B. Sidestream Gas Measurement System Configured to Communicate with a Mainstream Gas Measurement System Rather than providing an interface unit to which any type of Gas Measurement System can connect, the present invention also contemplates providing a sidestream Gas Measurement System capable of communicating with a Host System that is configured to interface solely with a mainstream Gas Measurement System. This is accomplished by providing a sidestream Gas Measurement System that is adapted to interface to a mainstream-only system by causing the sidestream Gas Measurement System to emulate the signals expected by a mainstream Gas Measurement System. In this manner, the sidestream Gas Measurement System can be used in conjunction with existing mainstream Gas Measurement Systems or with a Host System specifically configured for mainstream-only communication.

Figure 6:
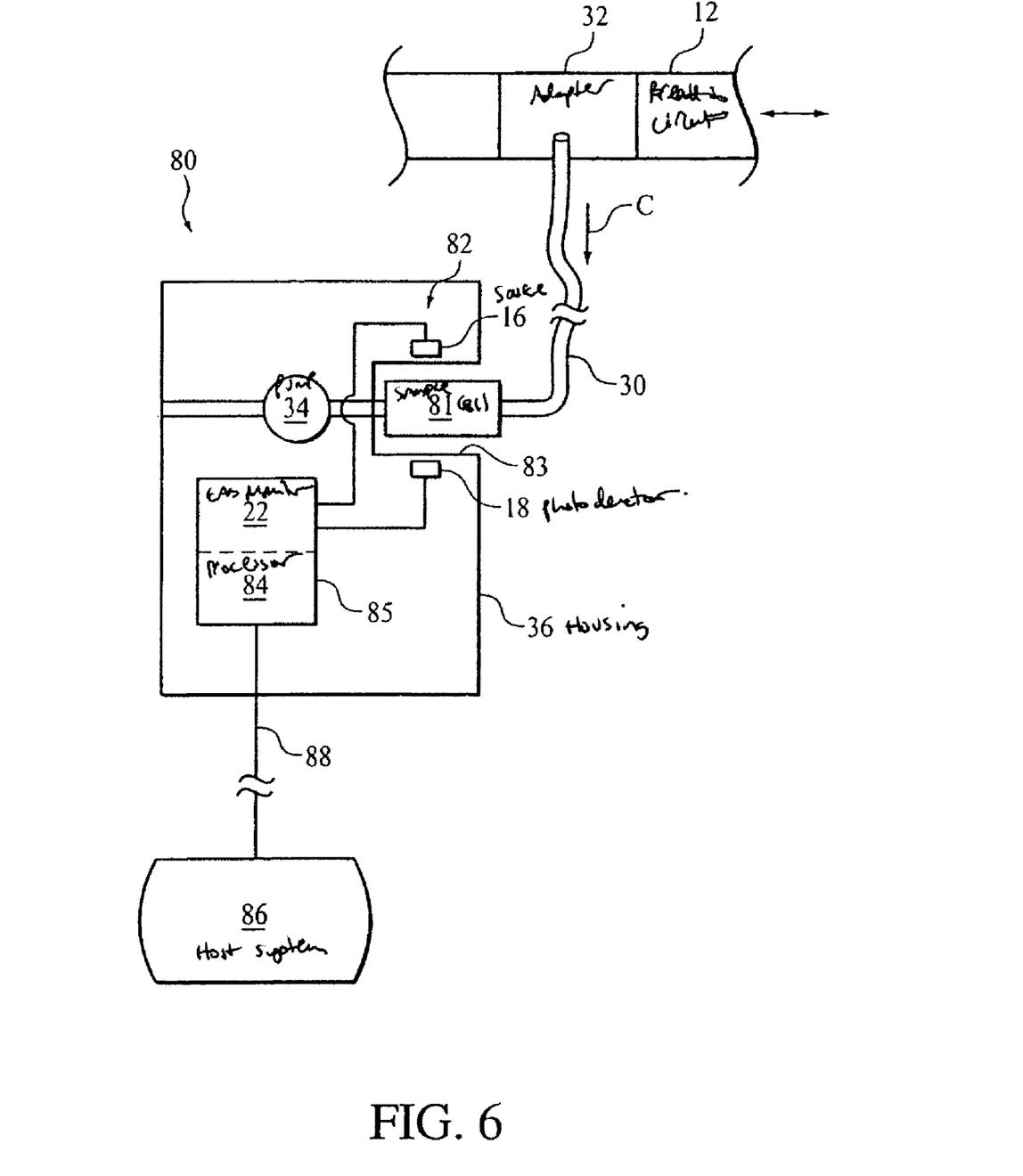
FIG. 6 is schematic diagram of an exemplary embodiment of a sidestream Gas Measurement System that emulates the signal protocol of a mainstream Gas Measurement System.

FIG. 6 schematically illustrates a sidestream Gas Measurement System 80 that is adapted to emulate the signal protocol of a mainstream Gas Measurement System. Sidestream Gas Measurement System 80 includes a Sample Cell 81 in fluid communication with an airway of a patient via tube 30. In this embodiment, Sample Cell 81 is selectively attachable to housing 36. More specifically, a Sample Cell connector 83 in the form of a receptacle is provided in housing 36 to allow the Sample Cell to selectively attach to the housing such that the Sample Cell is in alignment with the components of a Gas Sensor 82 provided in the housing. An adapter 32 is connected in line in breathing circuit 12 to connect tube 30 to the breathing circuit. Of course, a nasal canula can be used as the gas collection element in place of adapter 32 so that the gas is taken directly at the patient's airway. The sample gas is continuously aspirated from the breathing circuit or the nasal canula through sampling tube 30, as indicated by arrow C, and into a Sample Cell 10'. A pump 34 is typically provided to draw the gas into the Sample Cell from the gas sample site.

As noted above, sidestream Gas Measurement System 80 includes Gas Sensor 82 in communication with Sample Cell 81 when the Sample Cell is properly attached to the housing via the Sample Cell connector. As is the case in a conventional sidestream system, Gas Sensor 82 outputs a signal indicative of a property of a gas in the Sample Cell. This signal is provided to a Gas Monitor 22, which processes the signal to determine a respiratory gas variable based on the signal. A processor 84 receives the respiratory gas variable and communicates it to a Host System 86 via a communication link 88. Communication link 88 is either hardwired or wireless, but is preferably configured to correspond to the communication link provided to a conventional mainstream Gas Measurement System so that an end of the communication link can plug into the coupling element of the conventional mainstream Gas Measurement System or a Host System specifically configured for mainstream-only communication. Processor 84 and Gas Monitor 22 may be configured into one processing system 85, as shown in FIG. 6, or each function can be provided by separate processing elements.

Processor 84 outputs the respiratory gas variable via communication link 88 in such a way so as to emulate the signal protocol that a mainstream Gas Measurement System uses to communicate with a Gas Sensor (i.e., the signal provided on cable 20 of FIG. 1) or to communicate with a Gas Sensor and Gas Monitor combination (i.e., the signal provided on communication link 58 of FIG. 3). Emulation of the signal/control and power interfaces of a mainstream Gas Measurement System by the sidestream Gas Measurement System enables the sidestream Gas Measurement System to be used with a Host System designed to communicate only with a mainstream Gas Measurement System without the need to make any hardware modifications to the host portion of the respiratory gas monitoring system. The present invention, therefore, allows the existing installed base of mainstream Gas Measurement Systems to integrate in a seamless fashion with the sidestream sampling capability without having to purchase a new module or monitor.

Mainstream Gas Measurement Systems typically require power to be provided to the Gas Sensor to heat the windows of the Sample Cell directly or indirectly to reduce condensation. Therefore, to emulate the power interface of the mainstream Gas Measurement System by a sidestream Gas Measurement System, it is required that the power supplied by the Gas Monitor or the Host System to the Gas Sensor for the intended purpose of heating the Sample Cell serve instead to provide power for the sidestream pump and the respective control electronics. Similarly, the control signals to regulate the signal to be interpreted as temperature must be provided by the sidestream Gas Measurement System to the Host System through the sensor interface.

In order for a continuous supply of power to be maintained to the pump and control electronics, the sidestream Gas Measurement System must provide a signal representative of a temperature that is high enough to prevent the Host System from generating an error condition in response to a temperature that appears to be below the operating range. At the same time, this signal must be below the nominal temperature intended for the mainstream Gas Measurement System or the Host System will reduce or cut off the power intended to heat the mainstream sensor thereby reducing or removing the power required to operate the pump and the respective control electronics.

To provide a temperature feedback signal sufficient to ensure continued operation of the respiratory gas monitoring system while providing adequate power to operate the sidestream Gas Measurement System, a fixed regulated voltage level, or a slow acting feedback circuit may be used. The feedback circuit must be filtered to react slowly in order to simulate the slow response of a heater in order to prevent the heater power from oscillating (or cycling up and down).

Emulation of the signal/control interface of a mainstream Gas Measurement System requires a means to translate adverse conditions in the sidestream Gas Measurement System into conditions the Host System will recognize as interfering or error conditions so that the Host System can detect these and alert the user. There are circumstances with both mainstream and sidestream Gas Measurement System operation where the Gas Monitor or the Host System needs to detect and alert the user to conditions that may interfere with the ability of the Gas Measurement System to measure the respiratory gas. In the case of the mainstream Gas Measurement System, these conditions generally include the presence of liquids in the airway such as condensed water and other contaminants. In the case of the sidestream Gas Measurement System, these conditions include the presence of such liquids or contaminants in the sample tubing that is in fluid communication with the airway and the sidestream Gas Measurement System. However, in the case of the sidestream Gas Measurement System, there exists an additional condition that may interfere with the system's operation, such as a leak or disconnection of the sampling tubing. To accomplish this detection and alerting function, the present invention provides the same feedback signals as generated by the mainstream Gas Measurement System to indicate when an interfering condition exists.

In the exemplary sidestream Gas Measurement System according to the principles of the present invention, a pressure sensor is provided to measure pressure drop near the Sample Cell of the sidestream Gas Measurement System, and a flow sensor consisting of a differential pressure sensor connected across a capillary tube is provided to measure the flow through the sampling tube are used by the control circuitry to detect the conditions that may interfere with the gas measurement. For example, an occlusion caused by the presence of contaminants in the sampling tube may be detected by a change in the flow as measured by the flow sensor. Also, a leak or disconnection of the sample tubing is detected by change in the pressure measurement in the Sample Cell by a pressure sensor. As these conditions do not occur in mainstream Gas Measurement Systems, the detection of either of these conditions are used to simulate a condition that does occur in mainstream Gas Measurement Systems, namely, contamination of the Sample Cell windows. With mainstream Gas Measurement Systems, contamination is detected optically by a reduction in the level of a reference optical signal, which is a measurement of transmitted light across the Sample Cell at a wavelength unaffected by the respiratory gas of interest. The present invention reduces the reference signal sent from the sidestream Gas Measurement System to the Host System whenever an interfering condition as described are detected.

The sidestream Gas Measurement System embodying the present invention can be connected directly to Host Systems designed to function with a mainstream type Gas Measurement System. In some Host Systems there may be certain calibration procedures that involve the use of an optical zero or reference cells, which are no longer needed with the use of sidestream Gas Measurement System. In addition, certain messages displayed by the Host System to alert the user to the presence of interfering conditions may be worded inappropriately for sidestream operation. A non-volatile memory device typically used in the mainstream Gas Measurement System to store calibration parameters and identification information is also used in the sidestream Gas Measurement System. The identifying information is encoded such that Host Systems would be able to determine the presence of a sidestream Gas Measurement System if the software in the Host System was so enabled it could remove access to non-applicable calibration procedures and can alter the wording of messages as appropriate.

It should be noted that the sidestream Gas Measurement System 80 can also be used in the configuration shown in FIG. 5. That is, the present invention contemplates that sidestream Gas Measurement System 80 can provide an output to an interface unit that is, in turn, connected to a Host System.

Similar emulation methods can also be employed to enable a mainstream Gas Measurement System to be connected to Host Systems designed to function with a sidestream Gas Measurement System. This is accomplished, for example, by interposing the roles of the various mainstream and sidestream interface requirements and by providing a self contained temperature control system for heating of the Sample Cell windows within the mainstream Gas Measurement System.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

Definition of Terms Used in the Specification

The following is a listing of the terms used in the above specification. This listing is intended to supplement and not replace the definition of the terms given above, as understood by those skilled in the art based on the context in which they are presented, but may serve to help clarify the intended meaning of each.

Sample Cell—A device configured to contain a static or dynamic gas sample and in which the concentration of a particular gas constituent in the gas sample is ascertained.

Gas Sensor—Gas constituent measuring components associated with a Sample Cell, such as an optical emitter and detector, that produce a detected signal indicative of the concentration of a gas constituent in the gas sample under evaluation. This detected signal is typically processed to produce an indication of the concentration of a particular gas constituent in the gas sample within the Sample Cell.

Gas Monitor—Device that contains the functionality, such as the processing elements, required to produce an indication of the concentration of a particular gas constituent in the gas sample within the Sample Cell based on the detected signal form the Gas Sensor.

Gas Measurement System—System that includes a Sample Cell, Gas Sensor, and Gas Monitor. It is to be understood that these components can be physically separated or separable from on another, or various combinations of components can be located in one unit. For example, in a conventional sidestream Gas Measurement System, the Gas Sensor and Gas Monitor are provided in a common housing with the Sample Cell being selectively attachable to the housing.

Host System—A system that receives from an output from a Gas Measurement System an indication of the gas constituent under evaluation. The present invention contemplates that the Host System uses this information in any one of a variety ways. For example, the Host System may display the indication of the designated gas as a waveform or as a value in partial pressure units, such as mmHg or concentration in units such as a percent (%). The Host System can use the indication to calculate other parameters, which can then be displayed or communicated to another system, such as a central station or an interface unit.

Gas Monitoring System—System that includes the Host System and the Gas Measurement System (Sample Cell, Gas Sensor, and Gas Monitor).

What is claimed is:

1. A monitoring system comprising:
an interface unit having a input coupling and an output;
a plurality of gas measurement systems, wherein each gas measurement system is adapted to be placed in fluid communication with an airway of a patient to measure at least one respiratory gas, wherein each gas measurement system has an output coupling that is adapted to be removable coupled to the input coupling of the interface unit, and wherein each gas measurement system includes processing means for determining, from the respiratory gas, at least one respiratory variable of such a patient and for providing an output to the interface unit via the output coupling;
a display coupled to the output of the interface unit, wherein the display is adapted to display the respiratory variable of such a patient provided by any one of the plurality of gas measurement systems.

2. The monitoring system of claim 1, wherein the plurality of gas measurements systems include a sidestream gas measurement system and a mainstream gas measurement system.

3. The monitoring system of claim 1, wherein the plurality of gas measurement system communicate with the interface unit by a hardwired communication link, a wireless communication link, or both.

4. The monitoring system of claim 1, further comprising a monitoring system adapted to monitor a physiological characteristic of a patient other than a respiratory variable, and wherein the interface unit is adapted to be coupled to the monitoring system.

5. The monitoring system of claim 4, wherein the monitoring system communicates with the interface unit by a hardwired communication link, a wireless communication link, or both.

6. A sidestream gas measurement system adapted to communicate with a host system that is configured to communicate with a mainstream gas measurement system, the sidestream gas measurement system comprising:
a housing;
a sample cell connector associated with the housing and adapted to receive a sample cell;
a gas sensor disposed in the housing relative to the sample cell connector so as to be in communication with the sample cell responsive to the sample cell being received in the sample cell connector, and wherein the gas sensor outputs a signal indicative of a property of a gas in the sample cell;
emulation means, receiving the signal from the gas sensor, and using the signal in an output signal to simulate signals of output by a mainstream gas measurement system; and
a communication element operatively coupled to the emulation means to interface the sidestream gas measurement system with such a host system.

7. The sidestream gas measurement system of claim 6, wherein the output signal of the emulation means communicates via a hardwired communication link or a wireless communication link to the mainstream gas measurement system.

8. A sidestream gas measurement system, comprising:
a first conduit having a first end adapted to be placed in fluid communication with a patient circuit and a second end;
a sample cell disposed at the second end of the first conduit;
a gas sensor operatively coupled to the sample cell, wherein the gas sensor outputs a signal indicative of a property of a gas;
a processing element adapted to receive the signal and to determine a respiratory gas variable based on the signal; and
a host system interface configured to communicate an output of the processor with a host system configured to interface with a mainstream gas measurement system, and wherein the processing element configures signals provided by the host system interface to emulate signals provided by a mainstream gas measurement system or portion thereof.

* * * * *